US010465293B2

(12) United States Patent
Miller et al.

(10) Patent No.: US 10,465,293 B2
(45) Date of Patent: Nov. 5, 2019

(54) DOSE-BASED END-POINTING FOR LOW-KV FIB MILLING TEM SAMPLE PREPARATION

(75) Inventors: Thomas G. Miller, Portland, OR (US);
Jason Arjavac, Hillsboro, OR (US);
Michael Moriarty, Portland, OR (US)

(73) Assignee: FEI Company, Hillsboro, OR (US)

( * ) Notice: Subject to any disclaimer, the term of this patent is extended or adjusted under 35 U.S.C. 154(b) by 1007 days.

(21) Appl. No.: 13/600,843

(22) Filed: Aug. 31, 2012

(65) Prior Publication Data

US 2014/0061032 A1  Mar. 6, 2014

(51) Int. Cl.
| | |
|---|---|
| *C23F 1/04* | (2006.01) |
| *G01N 1/32* | (2006.01) |
| *H01J 37/302* | (2006.01) |
| *H01J 37/305* | (2006.01) |

(52) U.S. Cl.
CPC ............... *C23F 1/04* (2013.01); *G01N 1/32* (2013.01); *H01J 37/3023* (2013.01); *H01J 37/3056* (2013.01); *H01J 2237/30466* (2013.01); *H01J 2237/31745* (2013.01)

(58) Field of Classification Search
CPC .......... C23F 1/04; G01N 1/32; H01J 37/3023; H01J 37/3056; H01J 2237/30466; H01J 2237/31745
See application file for complete search history.

(56) References Cited

U.S. PATENT DOCUMENTS

| | | | | |
|---|---|---|---|---|
| 5,086,015 | A * | 2/1992 | Itoh | H01L 21/76802 |
| | | | | 148/DIG. 46 |
| 6,039,000 | A * | 3/2000 | Libby | H01J 37/3005 |
| | | | | 118/723 E |
| 7,700,367 | B2 * | 4/2010 | Fujii | G01N 1/32 |
| | | | | 436/174 |
| 7,880,151 | B2 * | 2/2011 | Wells | H01J 37/3056 |
| | | | | 250/307 |
| 8,170,832 | B2 | 5/2012 | Young et al. | |
| 2001/0053605 | A1 | 12/2001 | Phaneuf et al. | |
| 2003/0153192 | A1 | 8/2003 | Suthar et al. | |
| 2004/0245464 | A1 | 12/2004 | Iwasaki et al. | |
| 2005/0012512 | A1 | 1/2005 | Kolachina et al. | |
| 2009/0135240 | A1 | 5/2009 | Phaneuf et al. | |

(Continued)

FOREIGN PATENT DOCUMENTS

| | | |
|---|---|---|
| CN | 101644642 A | 2/2010 |
| WO | PCT/GB2010/000599 | * 10/2010 |
| WO | 2014014446 | 1/2014 |

*Primary Examiner* — Michael A Band

(57) ABSTRACT

A method, system, and computer-readable medium for forming transmission electron microscopy sample lamellae using a focused ion beam including directing a high energy focused ion beam toward a bulk volume of material; milling away the unwanted volume of material to produce an unfinished sample lamella with one or more exposed faces having a damage layer; characterizing the removal rate of the focused ion beam; subsequent to characterizing the removal rate, directing a low energy focused ion beam toward the unfinished sample lamella for a predetermined milling time to deliver a specified dose of ions per area from the low energy focused ion beam; and milling the unfinished sample lamella with the low energy focused ion beam to remove at least a portion of the damage layer to produce the finished sample lamella including at least a portion of the feature of interest.

28 Claims, 9 Drawing Sheets

(56) References Cited

U.S. PATENT DOCUMENTS

| | | | |
|---|---|---|---|
| 2009/0256081 A1* | 10/2009 | Kaga | H01J 37/12 |
| | | | 250/396 R |
| 2010/0006754 A1* | 1/2010 | Zhang | G01N 1/286 |
| | | | 250/307 |
| 2010/0300873 A1* | 12/2010 | Blackwood | G01N 1/32 |
| | | | 204/192.33 |
| 2012/0067718 A1* | 3/2012 | Cox | G01N 1/286 |
| | | | 204/192.33 |
| 2013/0105302 A1 | 5/2013 | Nanri et al. | |
| 2013/0143412 A1 | 6/2013 | Moriarty et al. | |

* cited by examiner

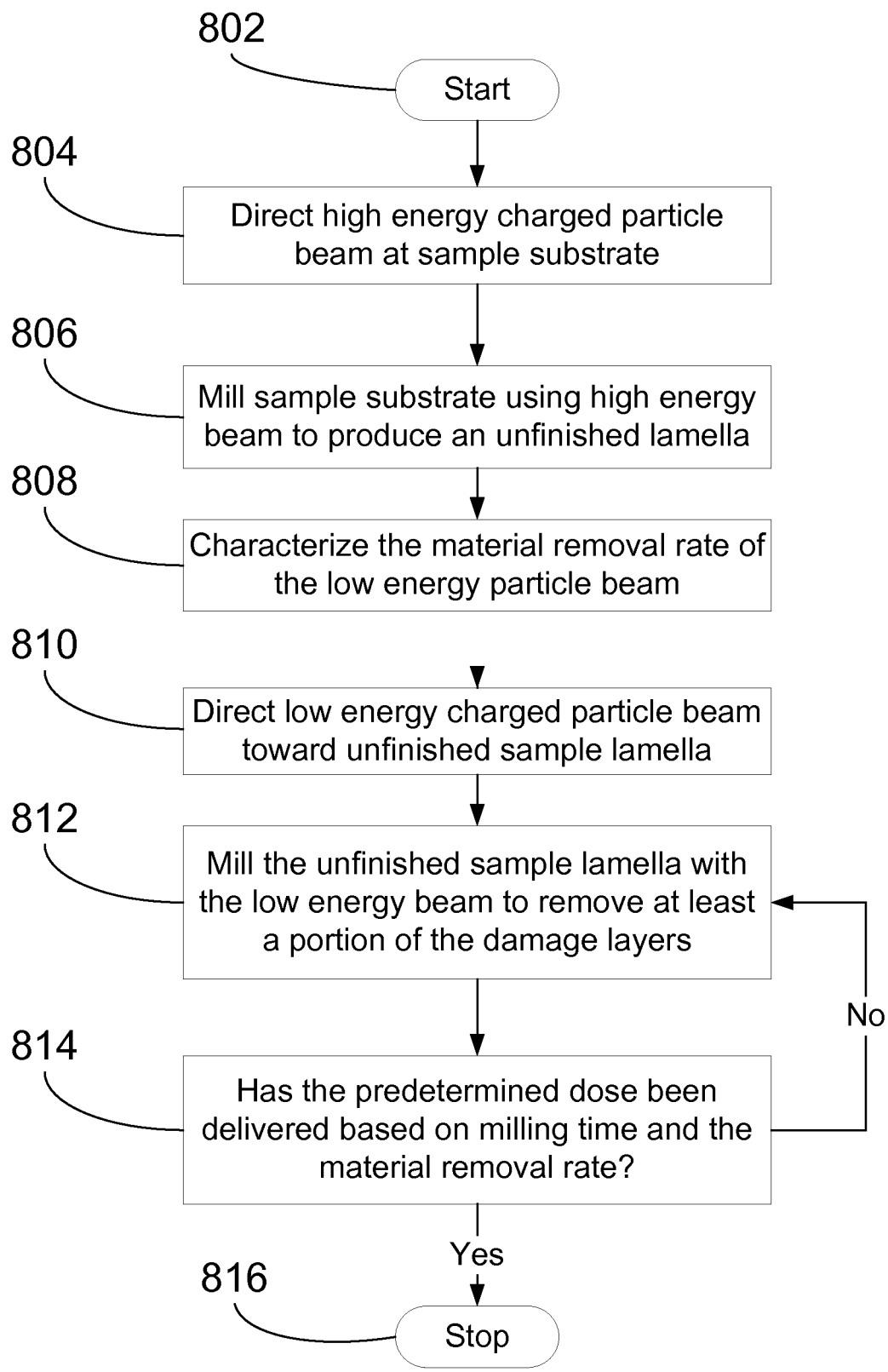

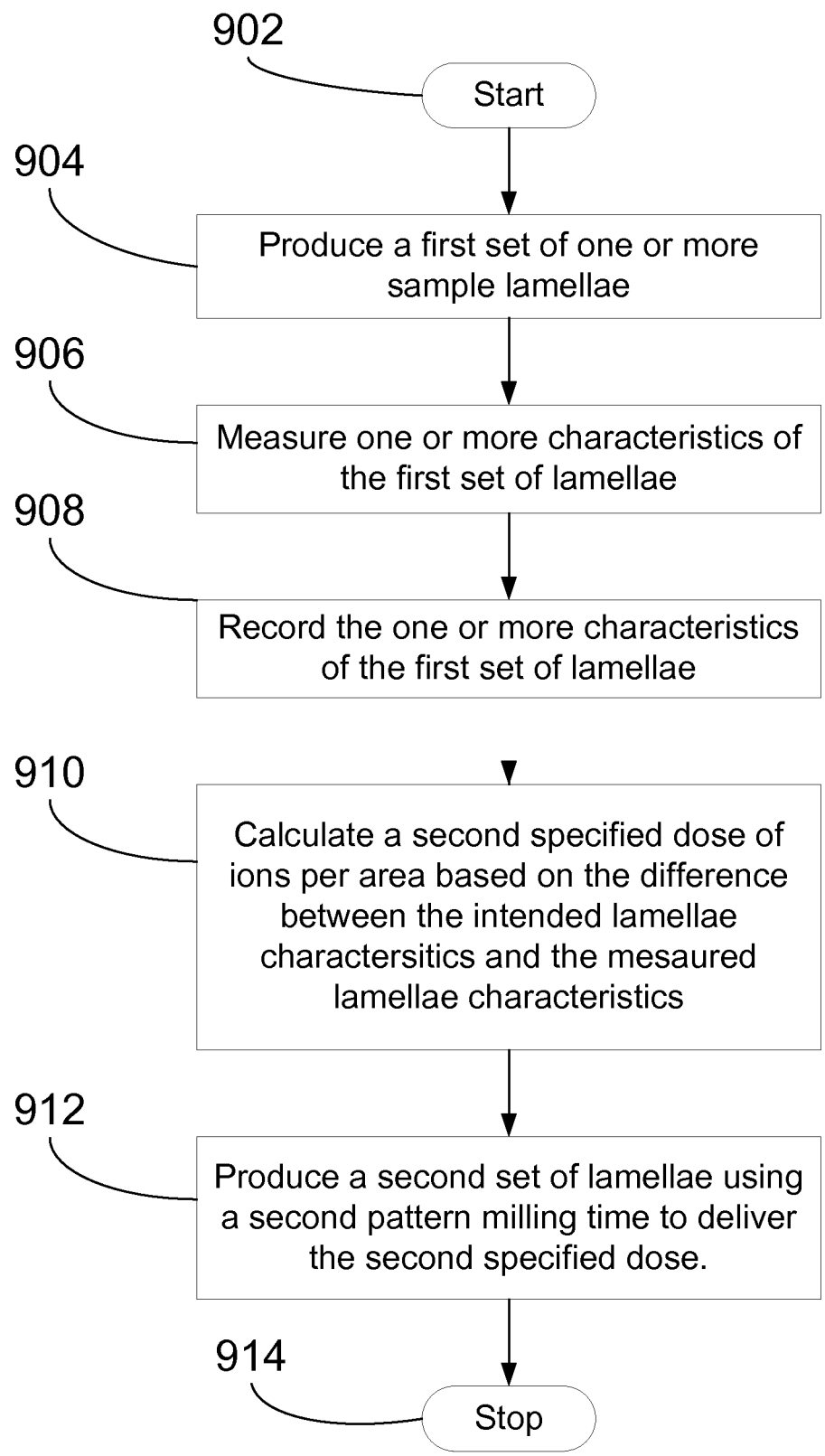

DOSE-BASED END-POINTING FOR LOW-KV FIB MILLING TEM SAMPLE PREPARATION

TECHNICAL FIELD OF THE INVENTION

The present invention relates to the preparation of samples for transmission electron microscopy (TEM) or scanning transmission electron microscopy (STEM), and in particular the use of charged particle beams in preparing TEM or STEM samples.

BACKGROUND OF THE INVENTION

Transmission electron microscopy (TEM) enables observers to form images of extremely small features, on the order of nanometers to fractions of Angstroms. TEM also allows analysis of the internal structure of a sample. In a TEM, a broad beam of electrons impacts the sample, and electrons that are transmitted through the sample are focused to form an image of the sample. The sample must be sufficiently thin to allow many of the electrons in the primary beam to travel though the sample and exit on the opposite site.

A related type of microscopy, scanning transmission electron microscopy (STEM) has similar requirements and capabilities.

A thin TEM sample cut from a bulk sample material is known as a "lamella". Lamellae are typically less than 100 nanometers (nm) thick, but for some applications a lamella must be considerably thinner. With advanced semiconductor fabrication processes at 30 nm and smaller, a lamella often needs to be less than 20 nm in thickness in order to avoid overlap among small scale structures. Thickness variations in the sample can result in lamella bending, overmilling, or other catastrophic defects. For such thin samples, lamella preparation is a critical step in TEM analysis that significantly determines the quality of structural characterization and analysis of the smallest and most critical structures.

Prior art methods for TEM lamella preparation typically make use of various milling operations performed by a focused ion beam (FIB) system. Such milling operations include cleaning cross-sections, regular cross-sections, and box mills placed in a manner such that the placement of the mill pattern determines final location of an edge of the lamella. The accuracy of lamella thickness and the final lamella center location were based on the accuracy of the placement of these FIB milling operations. In an automated work flow, all milling is typically performed with respect to some feature or fiducial on the top surface of the substrate from which the TEM sample lamella is to be milled.

A known issue involving the production of lamellae in crystalline materials (silicon is a commercially important example) is that a high energy focused ion beam (e.g., 30 kiloelectron volts (keV)) produces a substantial damage layer in the final lamella. The damage layer is caused, for example, by high energy ions discrupting the crystalline lattice of the sample. A known solution is to perform some final processing steps at lower FIB energy, typically 2 keV to 5 keV, but in general not more than 8 keV. These lower FIB energy processing steps are often referred to as "damage removal" steps. In some cases, even lower landing energies (less than 2 keV) are used. In general, the lower the landing energy, the less the disruption of the crystalline lattice and the resulting damage layer thickness decreases with lowered landing energy.

Low landing energy operation is also sometimes referred to as low-kV operation because, if the sample is at ground potential, then the landing energy is directly related to the high voltage potential on the ion source tip.

A problem associated with low-kV (kilovolt) damage removal procedures is that FIB resolution and probe characteristics are substantially degraded at low-kV. The FIB resolution and probe characteristics are degraded because chromatic aberrations typically result in substantial degradations in probe forming performance at low-kV.

This means all steps involving imaging, such as steps used to place the final low-kV damage removal mills, have degraded capability. Typically lamellae are created in automated processes where the placement of low-kV mills critically impacts the final cut placement and thickness precision. The end result is that the control of the placement of edges is much better at 30 kV then it is at low kV, and the process of damage removal introduces undesirably large amounts of uncertainty into thickness and position of the final lamella.

SUMMARY OF THE INVENTION

An exemplary embodiment of the present invention comprises a method for forming a transmission electron microscopy sample lamella using a focused ion beam. The method includes directing a high energy focused ion beam toward a bulk volume of material, the bulk volume of material including a feature of interest and an unwanted volume of material, to mill away the unwanted volume of material; milling away the unwanted volume of material with the high energy focused ion beam to produce an unfinished sample lamella having a thickness that is greater than the desired thickness of a finished sample lamella, one or more exposed faces of the unfinished sample lamella including a damage layer; characterizing the material removal rate of a low energy focused ion beam at a specified time prior to directing the low energy focused ion beam toward the unfinished sample lamella; subsequent to characterizing the material removal rate of the low energy focused ion beam, directing the low energy focused ion beam toward one or more of the exposed faces of the unfinished sample lamella for a predetermined pattern milling time to deliver a specified dose of ions per area from the low energy focused ion beam; and milling one or more of the exposed faces of the unfinished sample lamella with the low energy focused ion beam to remove at least a portion of the damage layer, thereby producing the finished sample lamella including at least a portion of the feature of interest.

Another exemplary embodiment of the present invention comprises a system for forming a transmission electron microscopy sample lamella. The system includes a focused ion beam column; a sample stage; a sample disposed on or within the sample stage; a programmable controller, the controller causing the system to automatically: direct a high energy focused ion beam toward a bulk volume of material, the bulk volume of material including a feature of interest and an unwanted volume of material, to mill away the unwanted volume of material; mill away the unwanted volume of material with the high energy focused ion beam to produce an unfinished sample lamella having a thickness that is greater than the desired thickness of a finished sample lamella, one or more exposed faces of the unfinished sample lamella including a damage layer; characterize the material removal rate of a low energy focused ion beam at a specified time prior to directing the low energy focused ion beam toward the unfinished sample lamella; subsequent to characterizing the material removal rate of the focused ion beam, direct the low energy focused ion beam toward one or more of the exposed faces of the unfinished sample lamella for a predetermined pattern milling time to deliver a specified dose of ions per area from the low energy focused ion beam; and mill one or more exposed faces of the unfinished sample lamella with the low energy focused ion beam to remove at least a portion of the damage layer, thereby producing the finished sample lamella including at least a portion of the feature of interest.

Another exemplary embodiment of the present invention comprises a non-transitory computer-readable medium encoded with a computer program for automatically forming a transmission electron microscopy sample lamella, the computer program comprising computer instructions that, when executed by a computer processor, cause a computer controlling a focused ion beam system to direct a high energy focused ion beam toward a bulk volume of material, the bulk volume of material including a feature of interest and an unwanted volume of material, to mill away the unwanted volume of material; mill away the unwanted volume of material with the high energy focused ion beam to produce an unfinished sample lamella having a thickness that is greater than the desired thickness of a finished sample lamella, one or more exposed faces of the unfinished sample lamella including a damage layer; characterize the material removal rate of the low energy focused ion beam at a specified time prior to directing the low energy focused ion beam toward the unfinished sample lamella; subsequent to characterizing the material removal rate of the low energy focused ion beam, direct the low energy focused ion beam toward one or more of the exposed faces of the unfinished sample lamella for a predetermined pattern milling time to deliver a specified dose of ions per area from the low energy focused ion beam; and mill the one or more exposed faces of the unfinished sample lamella with the low energy focused ion beam to remove at least a portion of the damage layer, thereby producing the finished sample lamella including at least a portion of the feature of interest.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 8 shows a flowchart depicting a low-kV method of forming a TEM sample lamella using dose-based end-pointing in accordance with one or more embodiments of the present invention.

FIG. 9 shows a flowchart depicting a method for using feedback from processed sites to improve performance of the final milling.

DETAILED DESCRIPTION OF PREFERRED EMBODIMENTS

Figure 1:
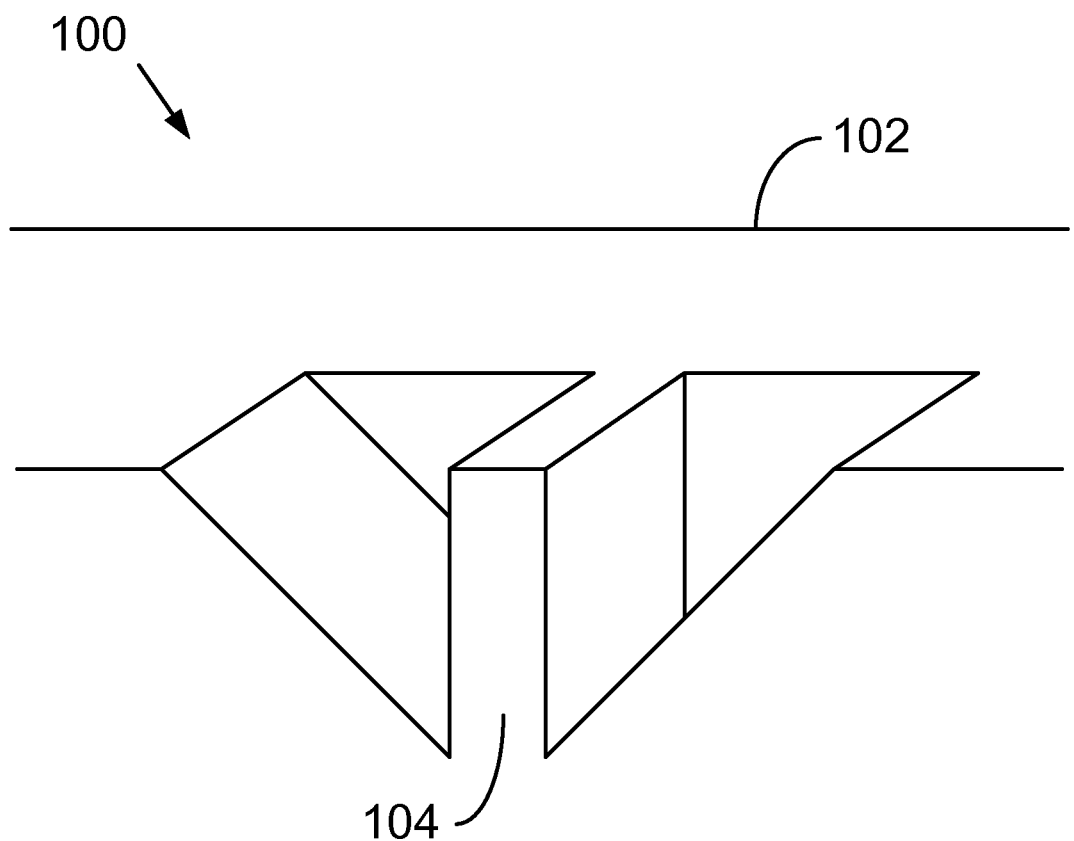
FIG. 1 shows a lamella 104 cut from a sample substrate 102 including a feature to be analyzed prior to the lamella being removed from the sample substrate.

Embodiments of the present invention are directed to methods and systems for forming sample lamellae utilizing low energy charged particle beam milling with dose-based end-pointing. Some embodiments of the present invention include fully automated methods and systems for forming sample lamellae utilizing low energy charged particle beam milling with dose-based end-pointing. Some embodiments of the present invention include methods and systems for forming sample lamellae utilizing automated steps and manual steps performed by an operator of the instrument. In at least one embodiment, the charged particle beam is a focused ion beam and the sample lamella is a transmission electron microscopy (TEM) lamella and/or scanning transmission electron microscopy (STEM) lamella. Standard high-kV (~30 kV) milling is performed with good accuracy of lamella edge placement. High-kV mills are placed with standard procedures, typically making use of fiducials on the substrate surface near a feature of interest, at least a portion of which is to be included in the finished sample lamella. High kV lamella thickness and placement is determined by fiducial accuracy issues as is known in the art.

After an accurate high-kV milling is finished, the lamella is properly located and is milled to a precisely controlled thickness. However the thickness of the lamella is slightly larger than the intended final thickness so that the damage layer caused by the high-kV milling can be removed with a final mill. In a preferred embodiment, the lamella is thicker than the desired final thickness of the lamella by a length approximately twice that of the penetration depth of the beam being used for high-kV milling. In the example of a 30 kV Gallium ion beam, that penetration depth is approximately 30 nm.

A dose-based approach is used to remove the damage layer. A final low-kV mill is performed with a pattern placed in a manner such that the accuracy of the placement of the mill is not important, only the final dose is important. In a preferred embodiment, a "box" mill is performed with size larger than the lamella area. In some cases the lamella being created will be extracted from a larger sample, such as a wafer, or piece of a wafer, in which there are structures near the top surface of the sample. In order to minimize certain types of undesirable artifacts associated with milling through these structures, it is desirable to have a significant angle between the incident beam and a ray normal to the top surface of the sample in the plane of the lamella face. It is typically desirable for this angle to be greater than thirty (30) degrees. In one embodiment, the FIB is directed at an angle that is substantially 45 degrees relative to the top surface of the sample. Other embodiments include an additional rotation of the FIB about the axis normal to the sample surface. Yet another embodiment includes compound angles involving both a substantial azimuthal and substantial polar angle of the ion beam relative to surface normal. These angles can be achieved in a variety of manner sometimes involving multi-axis stages, and sometimes involving movable columns or columns with the desired fixed orientation.

An additional aspect of embodiments of the present invention includes providing an accurate characterization of the removal rate of material on the lamella face and performing a time-controlled low-kV mill based on the characterization of the material removal rate. In some embodiments, the removal rate of material on the lamella face is characterized by determining an accurate dose of the charged particles delivered by the low-kV beam based on accurate calibration of the beam current. The accurate calibration of the beam current accounts for variations in beam current that occur over time. The delivered dose of charged particles is a function of the scanned area, the time spent scanning, and the beam current used while scanning. Typically the largest uncertainty is associated with the ion beam current. To provide good control of the dose, the beam current is measured at regular intervals or within a predetermined time proximity to the dose-based mill. This measurement can be performed at any specified time prior to the lamella preparation. For example, the specified time for the measurement can be a fraction of a second prior to the start of a mill, a minute prior to the start of a mill, once per day, once per week, once per wafer, etc. Methods of calibrating the FIB current generally consist of directing the ion beam into a collection electrode through which an accurate current measurement can be made by means of accurate current measurement electronics. This measurement can be done inside the ion column, or at a location exterior to the ion column.

Control of removed material is not dependent on low-kV imaging or pattern recognition, but purely on accurate control of the final dose. Careful measurement of FIB beam current immediately prior to milling (e.g., to no more than 1% error in beam current) and careful control of mill timing (e.g., to no more than 1% timing error) leads to an error in the amount of material removed from the unfinished lamella that is no more than 2%. In an exemplary case where 30 nm of material is removed from each side of the unfinished lamella, control of the milling error to no more than 2% limits the errors introduced by the low-KV mill to less than a nanometer. The numbers used in this paragraph are purely for illustrative purpose.

Calibrating the beam current is not the only way to characterize the material removal rate. In some embodiments of the present invention, characterization of the removal rate is performed by experimentally measuring the material removal rate at low-kV for the beam conditions being used. For example, a low-kV mill can be experimentally performed to determine that, for a given set of beam conditions, 1 nm of material is being removed from the lamella face per minute. The experimentally measured characterization of the material removal rate can be performed at any specified time prior to the lamella preparation. For example, the specified time for the measurement can be a fraction of a second prior to the start of a mill, a minute prior to the start of a mill, once per day, once per week, once per wafer, etc.

In another preferred embodiment of the invention, feedback from processed sites may be combined with the timing and dose control or may be used to determine suitable values for timing and dose. For example, during the production of one or more lamellae according to embodiments of the present invention, an accurate record is made of how much dose was delivered to each lamella during its production based on the careful control of mill timing and monitoring of the actual beam current during production of the lamellae. The lamellae are subsequently reviewed to determine how well the processing achieved its target objective and this information is feed back into the system to adjust the target dose for the production of additional lamellae. This review may be performed by any practical method, including a SEM image in the system inside the tool used for the low kV thinning or information collected from the TEM or STEM system that produces the final image of the lamella. A machine vision algorithm can be used to measure the characteristics of the lamella to calculate an adjustment factor to be used in determining subsequent doses.

In another example, the system processes multiple samples through the completion of the high-kV operations. Then the system applies the low-kV thinning operation to a subset of the samples and collects the same pieces of information as the above example. The tool collects SEM images of the completed lamella and a person reviews the result for quality. The person can indicate what scale factor should be delivered to the remaining sites. Alternatively, a machine vision algorithm can be used to measure the characteristics of the lamella to calculate an adjustment factor to be used in determining subsequent doses. When subsequent lamellae are produced, the information based on the SEM image review is combined with the new actual measured beam current on the preparation tool to reduce the actual dose per area delivered to more accurately achieve the target sample thickness.

Embodiments of the present invention are particularly useful for forming TEM sample lamella from a single-crystalline material, such as silicon. Single crystal substrates suffer more damage during high-kV milling than substrates that are not formed from a single crystal, such as those used in data storage applications.

FIG. 1 shows an unfinished lamella 104 cut from a sample substrate 102 prior to the lamella being removed from the sample substrate. Unfinished lamella 104 is formed by milling material away from sample substrate 102 in locations surrounding the lamella. The material is milled using a charged particle beam, such as an ion beam, an electron beam, or a laser beam. In a preferred embodiment, the charged particle beam is a focused ion beam. One or more fiducials (not shown) on sample substrate 102 can be used to locate the desired lamella location. A high-kV mill is initially performed with good accuracy of lamella edge placement. A high-kV mill removes material from the sample substrate using a beam of charged particles having an energy greater than 8 keV, preferably around 30 keV.

Figure 2:
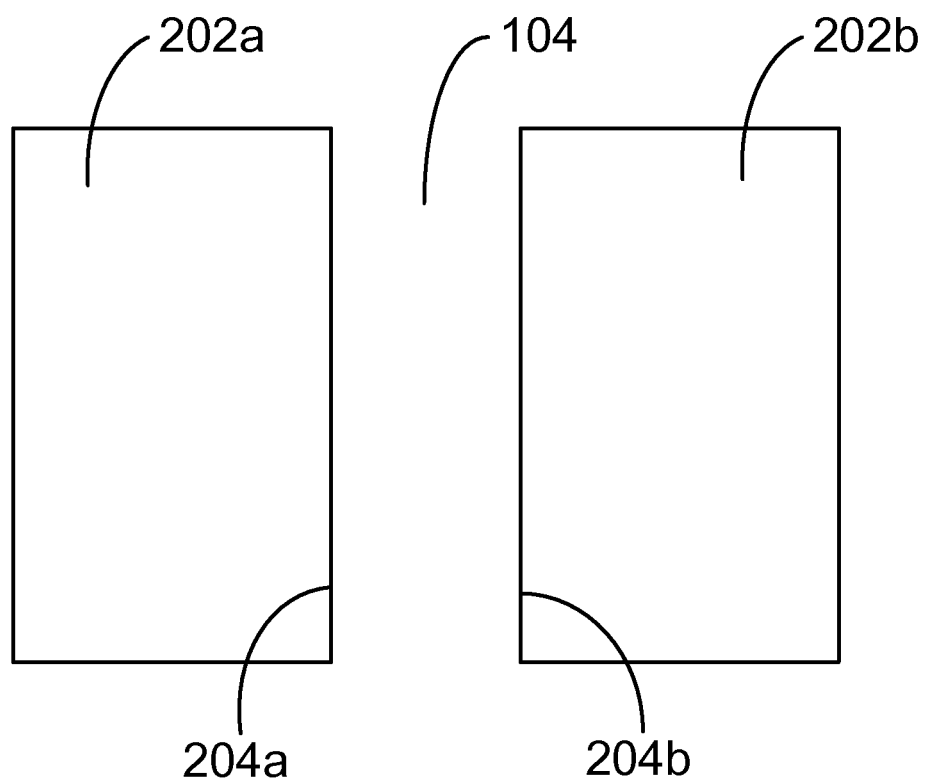
FIG. 2 shows a top view of lamella 104 cut from sample substrate 102 prior to the lamella being removed from the sample substrate.

FIG. 2 shows a top view of unfinished lamella 104 after performing the initial high-kV milling. The charged particle beam removes substrate material from high-kV mill areas 202*a-b* to expose vertical lamella faces 204*a-b*. High-kV mill areas 202*a-b* are located on either side of lamella 104. One or more fiducials (not shown) may be used determine the location of high-kV mill areas 202*a-b* on the sample substrate. As a consequence of the high-kV milling used to remove the material from high-kV mill areas 202*a-b*, unfinished lamella 104 includes damage layers that need to be corrected or removed before the lamella can be analyzed, for example, by a TEM.

Figure 3:
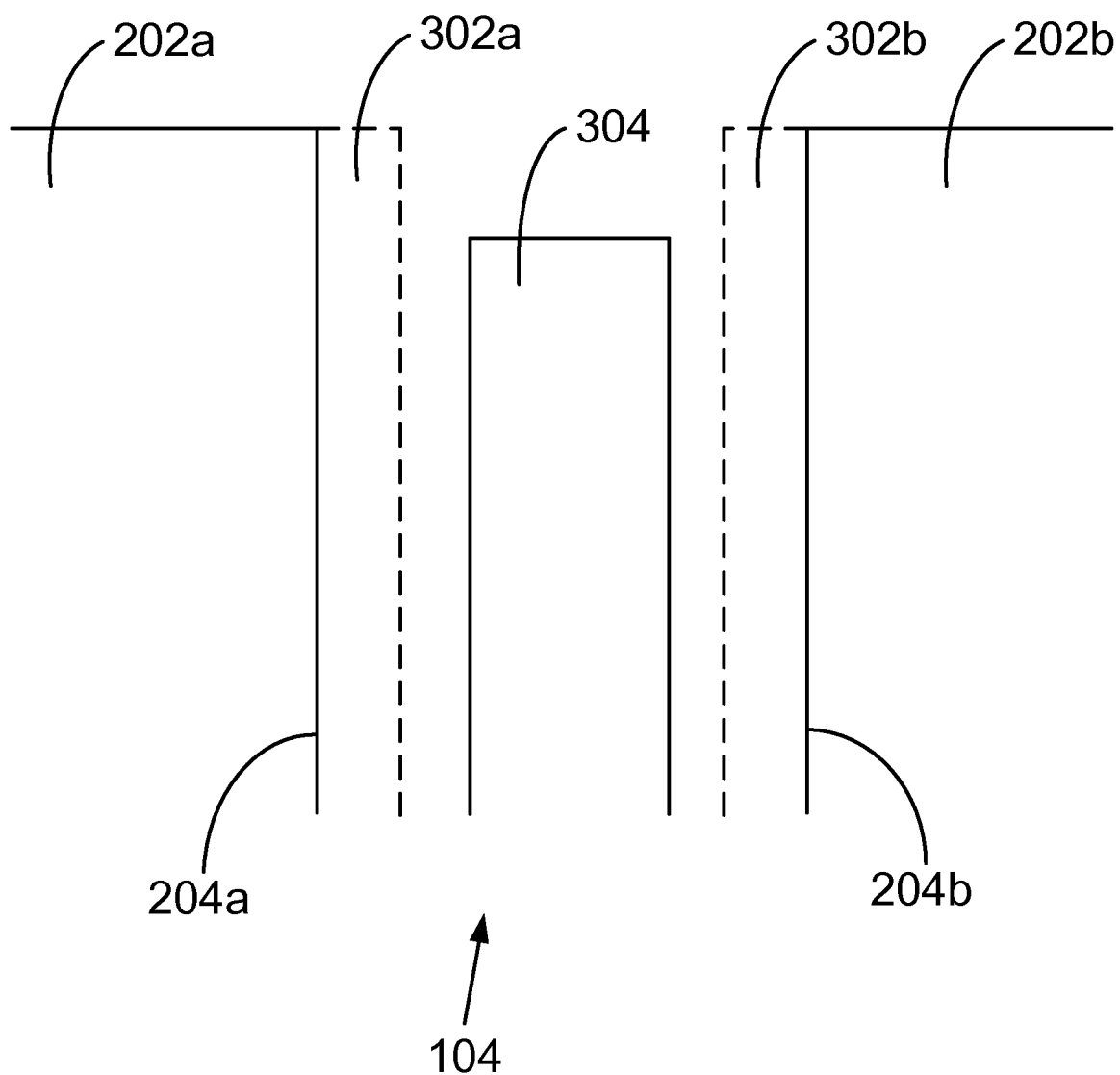
FIG. 3 shows a top view of one end of unfinished lamella 104, including damage layers 302a-b and the location of final lamella 304.

FIG. 3 shows a top view of one end of unfinished lamella 104, including damage layers 302*a-b* and the location of final lamella 304. Damage layers 302*a-b* extend from lamella faces 204*a-b* to a certain depth within unfinished lamella 104. To allow for the removal of the damage layers in a subsequent low-kV milling step, the high-kV milling step is performed so that unfinished lamella 104 has a thickness that is larger than the intended thickness of final lamella 304. In one or more embodiments, the high-kV mill is performed so that each side of lamella 104 is substantially 30 nanometers (nm) thicker than the intended thickness for that side of finished lamella 304.

Damage layers 302*a-b* result from the initial high-kV milling of unfinished lamella 104. Milling with a high energy charged particle beam has the benefit of higher mill rates and more accurate beam placement because chromatic aberration is reduced. But higher energy particles also cause damage to the sample substrate, producing damage layers 302*a-b*. For example, high-kV milling of a silicon crystal substrate with a focused ion beam can cause unwanted damage to the crystal lattice. Therefore, embodiments of the present invention include performing a final mill to remove damage layers 302*a-b*. The final milling step is a low-kV mill that utilizes dose-based end-pointing.

Figure 4:
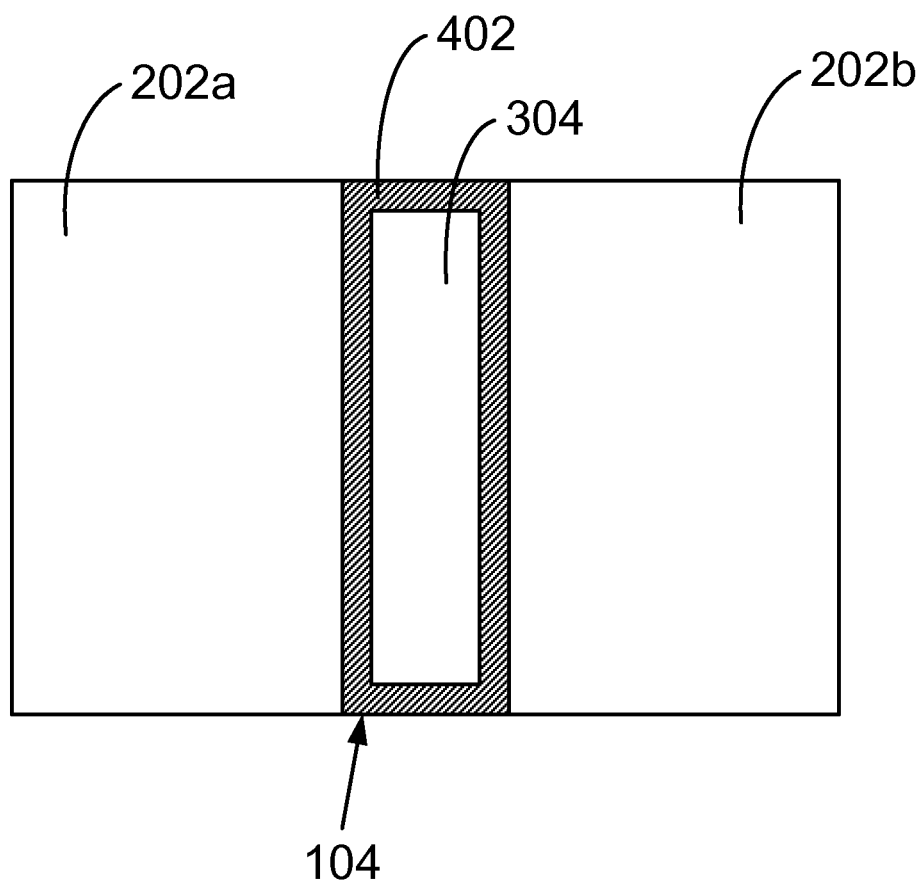
FIG. 4 shows a top view of unfinished lamella 104 and the placement of exemplary low-kV milling area 402 to perform a final mill.

FIG. 4 shows a top view of unfinished lamella 104 and the placement of exemplary low-kV milling area 402 to perform a final mill. Low-kV mill area 402 is placed in a manner such that the accuracy of the placement is not important, only the final dose of particles is important. Preferably, a box mill is performed around unfinished lamella 104 with a size larger than the intended final thickness of finished lamella 304. The simplest type of box mill is one in which a serpentine or raster pattern is traced across a defined geometric shape, typically a rectangle, with many repetitions of the pattern being traced out over the duration of the mill. For the purpose of this invention, the key concept is that a box mill is differentiated from a cleaning cross section mill in that mills of the style of a cleaning cross section have a location of milling that is slowly progressing. For the purpose of this invention the exact details of the box mill pattern are not important, for example pattern could be traced out across a defined area that is substantially circular. Low-kV mill area 402 includes substantially all of damage layers 302*a-b* so that upon the completion of the low-kV milling operation substantially all of the damage layers 302*a-b* are removed from finished lamella 304. Because low-kV milling is used instead of high-kV milling, damage to finished lamella 304 is eliminated or significantly reduced compared to the damage to unfinished lamella 304 caused by the high-kV milling.

Figure 5:
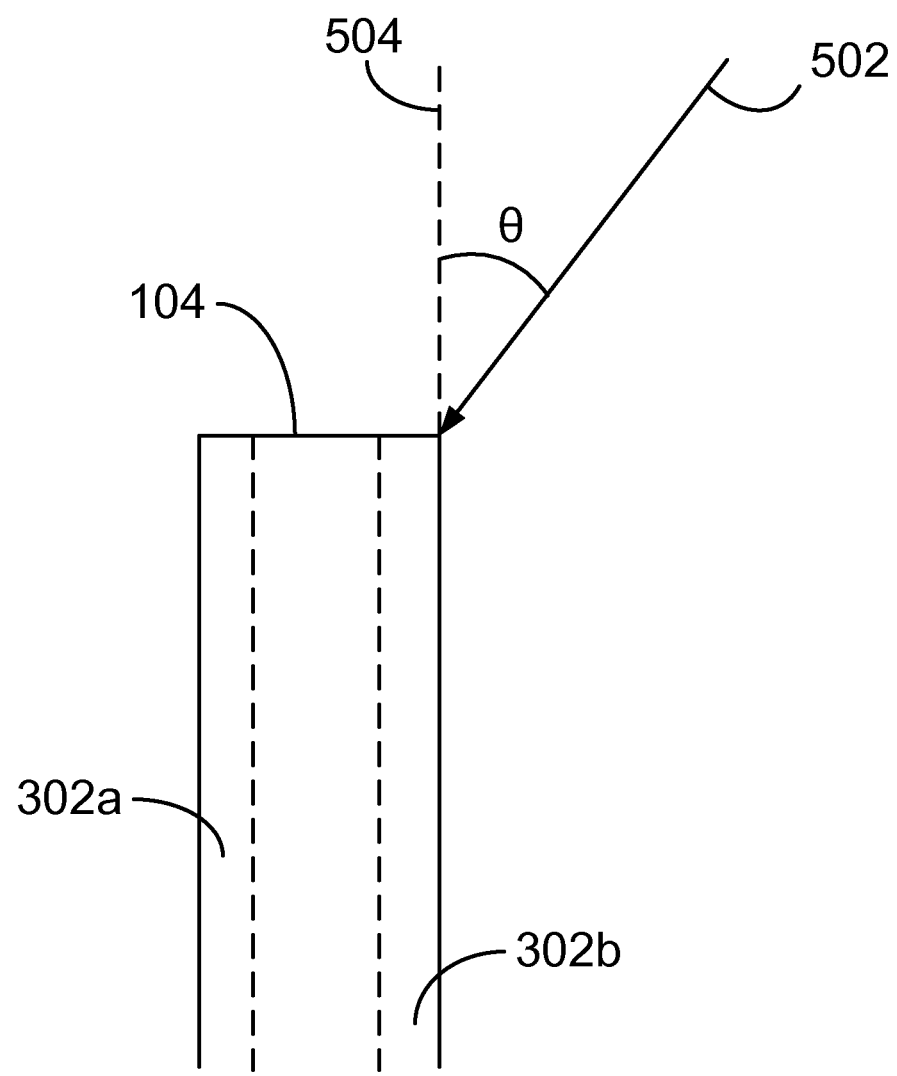
FIG. 5 shows a side view of unfinished lamella 104 during low-kV milling.

FIG. 5 shows a side view of unfinished lamella 104 during low-kV milling. Performance can be improved by operating the charged particle beam 502 in a manner that is not substantially "top-down". In some cases lamella 104 will be extracted from a larger sample, such as a wafer, or piece of a wafer, in which there are structures near the top surface of the sample 102. In order to minimize certain types of undesirable artifacts associated with milling through these structures, it is desirable to have a significant angle (θ) between the incident beam and a ray 504 normal to the top surface of the sample in the plane of the face of lamella 104. It is typically desirable for angle θ to be greater than thirty (30) degrees. In one embodiment, the FIB is directed at an angle θ that is substantially 45 degrees relative to the top surface of the sample.

Figure 6:
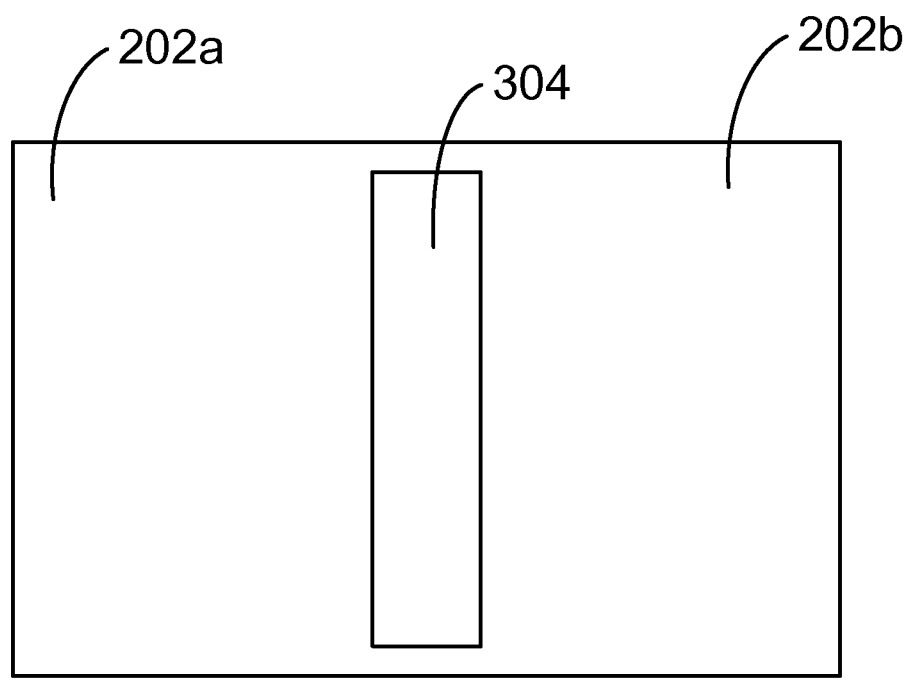
FIG. 6 shows a top down view of finished lamella 304.

FIG. 6 shows a top down view of finished lamella 304. Substantially all of damage layers 302*a-b* are removed from finished lamella 304 by performing low-kV milling. Finished lamella 304 may still be attached at its base to sample substrate 102. Further processing, such as undercutting, may be performed to separate lamella 304 from the sample substrate for analysis in another instrument.

FIG. 8 shows a flowchart depicting a low-kV method of forming a TEM sample lamella using dose-based end-pointing in accordance with one or more embodiments of the present invention. The method starts at 802 and proceeds to step 804, where a high energy charged particle beam is directed at sample substrate 102. The high energy charged particle beam is directed at sample substrate 102 to perform a high-kV milling operation. The high-kV milling operation uses the high energy beam to remove an unwanted volume of bulk substrate material from high-kV mill areas 202*a-b* to expose vertical lamella faces 204*a-b* of unfinished lamella 104 (step 806). The high energy charged particle beam has landing energies greater than 8 keV, and preferably around 30 keV.

Prior to performing damage removal with a low energy beam, the material removal rate of the low energy charged particle beam is characterized (step 808). The characterization of the removal rate can be accomplished by accurately measuring the beam current to determine a calibrated beam current, by experimentally measuring the material removal rate of the low energy beam, or any other suitable method for characterizing the removal rate of the low energy beam. If the removal rate is characterized by measuring the beam current, then the dose of charged particles is controlled by accurate calibration of the beam current to account for day to day (or even more frequent) variation in beam current. In one embodiment of the present invention, the beam current measurement of step 808 is performed immediately prior to performing the low-kV milling steps. Alternatively, the beam current measurement of step 808 can be performed at regularly space time intervals. Methods of calibrating the beam current include, but are not limited to, blanked beam measurements with a calibrated picoammeter and measurements of beam current using a stage Faraday cup.

After milling unfinished lamella 104 with a high energy charged particle beam and characterizing the material removal rate, a low energy charged particle beam is directed toward unfinished lamella 104 (step 810). The low energy particle beam has landing energies of less than 8 keV, and preferably between 2 keV and 5 keV. The low energy charged particle beam is directed at unfinished lamella 104 to perform a low-kV milling operation. The low-kV milling operation uses the low energy beam to remove damage layers 302*a-b* (step 812). The low-kV milling step is precisely timed so that a predetermined dose of charged particles is delivered based on the milling time and the material removal rate (step 814). When the predetermined dose of charged particles has been delivered, the method stops at terminator 816. The finished sample lamella includes at least a portion of the feature of interest.

Control of the removed material is not dependent upon low-kV imaging or pattern recognition, but purely on the accurate control of the final dose. The final dose in controlled by accurate characterization of the material removal rate at a specified time prior to milling and careful control of the timing of the mill. In a preferred embodiment, timing error is controlled to less than one percent (1%) and error in beam current is controlled to less than one percent (1%). This leads to an error in material removed that is less than two percent (2%). For example, if thirty nanometers (30 nm) of material is removed on each side of unfinished lamella 104, control of material removed to less than 2% allows for sub-nanometer errors introduced by the low-kV milling operation.

Embodiments of the present invention are described herein with respect to forming TEM lamellae. One skilled in the art will recognize that embodiments of the present invention are not only limited to forming TEM lamellae, but also apply to forming other types of lamellae, such as STEM lamellae.

In preferred embodiments, the method of FIG. 8 is fully automated and the final end-pointing of finished lamella 304 does not require any human interaction, in particular any human visual interaction. The beam current is measured immediately prior to the low-kV milling steps and the low-kV milling time is adjusted based on the most recent beam current calibration to give extremely accurate dose control. The milling pattern is placed in a manner so as to "over-expose" the region around the region of interest such that the position of the placement has little or no impact to the material removed from the region of interest.

FIG. 9 shows a flowchart depicting a method for using feedback from processed sites to improve performance of the final milling. In this embodiment of the invention, feedback from processed sites may be combined with the timing and dose control or may be used to determine suitable values for timing and dose. The method begins start block 902 and proceeds to step 904. A first set of one or more lamellae are produced according the method shown in FIG. 8. An accurate record is made of how much dose was delivered to each lamella during step 904 based on the careful control of mill timing and monitoring of the actual beam current during production of the lamellae. The lamellae are subsequently reviewed to determine how well the processing achieved its target objective. One or more characteristics of the lamellae are measured either while the lamellae are being milled or at a point in time after the milling of the lamellae is complete (step 906). The one or more characteristics of the lamellae are recorded (step 908), such as lamella thickness, the size of the remaining damage layer, an error offset in mill placement, etc. A second specified dose of ions per area for the low energy focused ion beam is calculated based on the difference between an intended lamella characteristic and the one or more measured characteristics of the first set of lamellae (step 910). This information is feed back into the system to adjust the target dose for the production of additional lamellae. This review may be performed by any practical method, including a SEM image in the system inside the tool used for the low kV thinning or information collected from the TEM or STEM system that produces the final image of the lamella. A second set of one or more sample lamellae is produced using a second pattern milling time to deliver the second specified dose of ions per area for the low energy focused ion beam (step 912). The process ends at terminator 914. This feedback process can be applied multiple times to improve the accuracy of the milling of the finished sample lamellae.

For example, using embodiments of the methods of FIGS. 8 and 9, the system producing the lamella collects the following pieces of information: (1) the sample was 95.0 nm thick prior to the start of the low-kV mill, (2) the low-kV mill operated at an acceleration voltage of 2 kV, (3) the low-kV mill applied to each side delivered to a target region with an area of 9.00 $\mu m^2$ for a duration of 35.7 seconds, and (4) the measured beam current at the time of the low-kV mill was 85.4 pA. The TEM system imaging the lamella determines that the sample thickness was 4% less than the optimal thickness. When subsequent lamellae are produced, the information from the TEM system is combined with the new actual measured beam current on the preparation tool to reduce the actual dose per area delivered to more accurately achieve the target sample thickness.

In another example, the system processes multiple samples through the completion of the high-kV operations. Then the system applies the low-kV thinning operation to a subset of the samples and collects the same pieces of information as the above example. The tool collects SEM images of the completed lamella and a person reviews the result for quality. The person can indicate what scale factor should be delivered to the remaining sites. When subsequent lamellae are produced, the information based on the SEM image review is combined with the new actual measured beam current on the preparation tool to reduce the actual dose per area delivered to more accurately achieve the target sample thickness.

Figure 7:
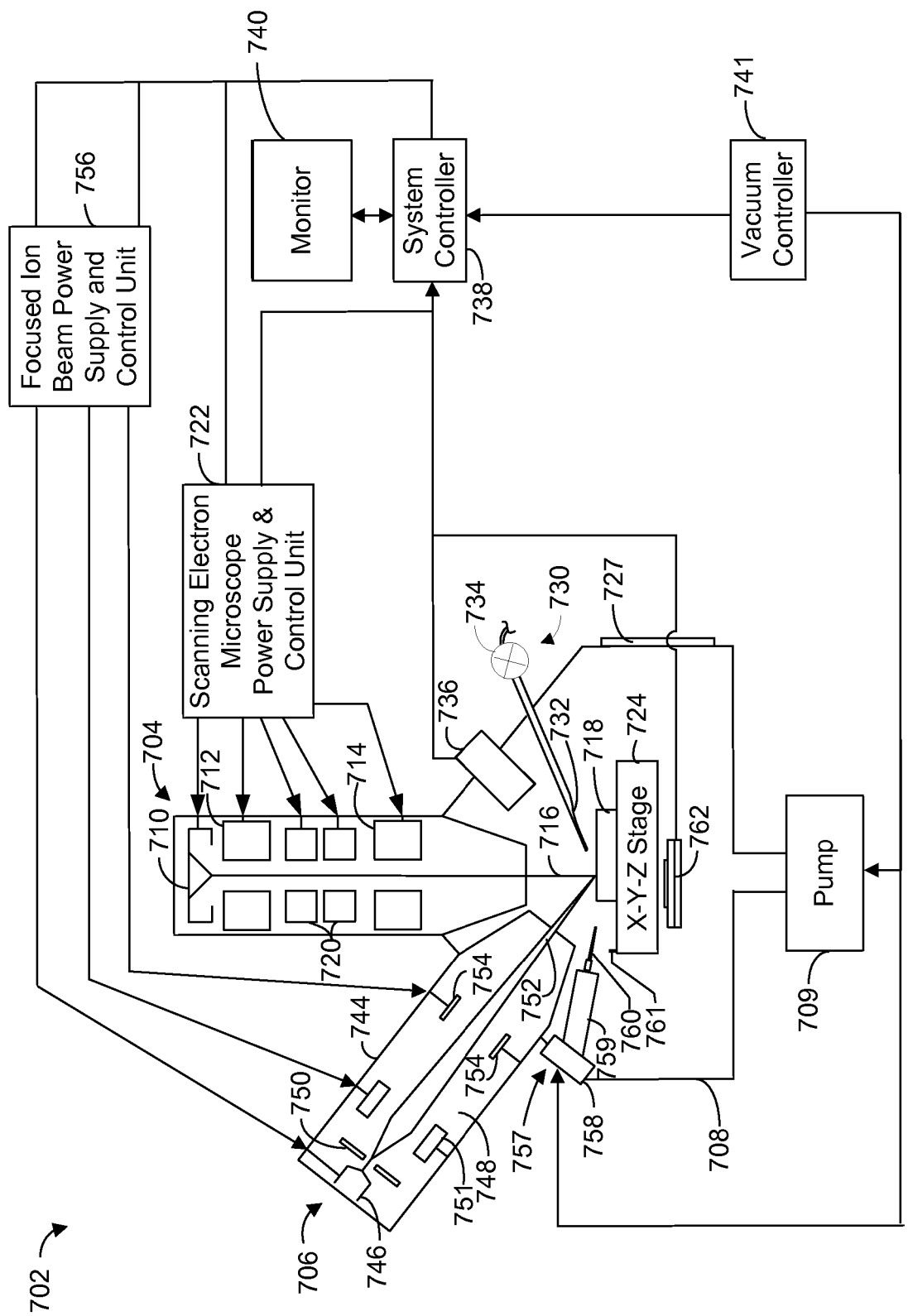
FIG. 7 shows one embodiment of an exemplary charged particle beam system 702 that is equipped to carry out embodiments of the present invention.

FIG. 7 depicts one embodiment of an exemplary dual beam SEM/FIB system 702 that is equipped to carry out embodiments of the present invention. The present invention does not require a dual beam system, and can be readily used with any charged particle beams system, including a single FIB system. The dual-beam system is described here for exemplary purposes only. Preparation and analysis of such a TEM sample can be performed in a dual beam electron beam/focused ion beam system such as the one now described. Suitable charged particle beam systems are commercially available, for example, from FEI Company, Hillsboro, Oreg., the assignee of the present application. While an example of suitable hardware is provided below, the invention is not limited to being implemented in any particular type of hardware.

Dual beam system 702 has a vertically mounted electron beam column 704 and a focused ion beam (FIB) column 706 mounted at an angle of approximately 52 degrees from the vertical on an evacuable specimen chamber 708. The specimen chamber may be evacuated by pump system 709, which typically includes one or more, or a combination of, a turbo-molecular pump, oil diffusion pumps, ion getter pumps, scroll pumps, or other known pumping means.

The electron beam column 704 includes an electron source 710, such as a Schottky emitter or a cold field emitter, for producing electrons, and electron-optical lenses 712 and 714 forming a finely focused beam of electrons 716. Electron source 710 is typically maintained at an electrical potential of between 500 V and 30 kV above the electrical potential of a work piece 718, which is typically maintained at ground potential.

Thus, electrons impact the work piece 718 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 718 may comprise, for example, a semiconductor device, microelectromechanical system (MEMS), data storage device, or a sample of material being analyzed for its material characteristics or composition. The impact point of the beam of electrons 716 can be positioned on and scanned over the surface of a work piece 718 by means of deflection coils 720. Operation of lenses 712 and 714 and deflection coils 720 is controlled by scanning electron microscope power supply and control unit 722. Lenses and deflection unit may use electric fields, magnetic fields, or a combination thereof.

Work piece 718 is on movable stage 724 within specimen chamber 708. Stage 724 can preferably move in a horizontal plane (X-axis and Y-axis) and vertically (Z-axis) and can tilt approximately sixty (60) degrees and rotate about the Z-axis. A door 727 can be opened for inserting work piece 718 onto X-Y-Z stage 724 and also for servicing an internal gas supply reservoir (not shown), if one is used. The door is interlocked so that it cannot be opened if specimen chamber 708 is evacuated.

Mounted on the vacuum chamber are one or more gas injection systems (GIS) 730. Each GIS may comprise a reservoir (not shown) for holding the precursor or activation materials and a needle 732 for directing the gas to the surface of the work piece. Each GIS further comprises means 734 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 716 strike work piece 718, secondary electrons, backscattered electrons, and Auger electrons are emitted and can be detected to form an image or to determine information about the work piece. Secondary electrons, for example, are detected by secondary electron detector 736, such as an Everhart-Thornley detector, or a semiconductor detector device capable of detecting low energy electrons. STEM detector 762, located beneath the TEM sample holder 761 and the stage 724, can collect electrons that are transmitted through a sample mounted on the TEM sample holder. Signals from the detectors 736, 762 are provided to a programmable system controller 738. Said controller 738 also controls the deflector signals, lenses, electron source, GIS, stage and pump, and other items of the instrument. Monitor 740 is used to display user controls and an image of the work piece using the signal. Said controller 738 may comprise a programmable general purpose computer including tangible, non-transitory computer-readable medium, the memory being encoded with computer instructions that, when executed by a processor of the computer causes the computer to automatically perform embodiments of the present invention, such as the method depicted in FIG. 8.

The chamber 708 is evacuated by pump system 709 under the control of vacuum controller 741. The vacuum system provides within chamber 708 a vacuum of approximately 7×10-6 mbar. When a suitable precursor or activator gas is introduced onto the sample surface, the chamber background pressure may rise, typically to about 5×10-5 mbar.

Focused ion beam column 706 comprises an upper neck portion 744 within which are located an ion source 746 and a focusing column 748 including extractor electrode 750 and an electrostatic optical system including an objective lens 751. Ion source 746 may comprise a liquid metal gallium ion source, a plasma ion source, a liquid metal alloy source, or any other type of ion source. The axis of focusing column 748 can be oriented at a non-zero angle from the axis of the electron column. An ion beam 752 passes from ion source 746 through focusing column 748 and between electrostatic deflectors 754 toward work piece 718.

FIB power supply and control unit 756 provides an electrical potential at ion source 746. Ion source 746 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 756 is coupled to deflection plates 754 which can cause the ion beam to trace out a corresponding pattern on the upper surface of work piece 718. In some systems, the deflection plates are placed before the final lens, as is well known in the art. Beam blanking electrodes (not shown) within ion beam focusing column 748 cause ion beam 752 to impact onto blanking aperture (not shown) instead of work piece 718 when a FIB power supply and control unit 756 applies a blanking voltage to the blanking electrode.

The ion source 746 typically provides a beam of singly charged positive gallium ions that can be focused into a sub one-tenth micrometer wide beam at work piece 718 for modifying the work piece 718 by ion milling, enhanced etch, material deposition, or for imaging the work piece 718.

A micromanipulator 757, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 757 may comprise precision electric motors 758 positioned outside the vacuum chamber to provide X, Y, Z, and theta control of a portion 759 positioned within the vacuum chamber. The micromanipulator 757 can be fitted with different end effectors for manipulating small objects. In the embodiments described herein, the end effector is a thin probe 760. As is known in the prior art, a micromanipulator (or microprobe) can be used to transfer a TEM sample (which has been freed from a substrate, typically by an ion beam) to a TEM sample holder 761 for analysis.

System controller 738 controls the operations of the various parts of dual beam system 702. Through system controller 738, a user can cause ion beam 752 or electron beam 716 to be scanned in a desired manner through commands entered into a conventional user interface (not shown). Alternatively, system controller 738 may control dual beam system 702 in accordance with programmed instructions. FIG. 7 is a schematic representation, which does not include all the elements of a typical dual beam system and which does not reflect the actual appearance and size of, or the relationship between, all the elements.

Although the description of the present invention above is mainly directed at methods of preparing ultra-thin TEM samples, it should be recognized that an apparatus performing the operation of such a method would further be within the scope of the present invention. Further, it should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Although much of the previous description is directed at semiconductor wafers, the invention could be applied to any suitable substrate or surface. Further, the present invention could be applied to samples that are thinned in the vacuum chamber but removed from the substrate outside the vacuum chamber (ex-situ-type samples) or to samples extracted from the substrate and thinned after mounting on a TEM grid inside the vacuum chamber (in-situ-type samples). Whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . " The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follow:

1. A method for forming a transmission electron microscopy sample lamella using a focused ion beam, the method comprising:

directing a high energy focused ion beam toward a bulk volume of material, the bulk volume of material including a feature of interest and a volume of material to be removed, to mill away the volume of material to be removed;

milling away the volume of material to be removed with the high energy focused ion beam to produce an unfinished sample lamella having a thickness that is greater than the desired thickness of a finished sample lamella, one or more faces of the unfinished sample lamella including a damage layer;

characterizing the material removal rate of a low energy focused ion beam by measuring the material removal rate of the low energy focused ion beam on a material;

subsequent to characterizing the material removal rate of the low energy focused ion beam, directing the low energy focused ion beam toward one or more of the exposed faces of the unfinished sample lamella for a predetermined pattern milling time to deliver a specified dose of ions per area from the low energy focused ion beam; and milling the one or more exposed faces of the unfinished sample lamella with the low energy focused ion beam to remove at least a portion of the damage layer, thereby producing the finished sample lamella having a planar surface and including at least a portion of the feature of interest; and wherein milling the one or more exposed faces of the unfinished sample lamella with the low energy focused ion beam includes performing a box mill around the unfinished sample lamella with a size that is larger than the intended final thickness of the finished sample lamella, the box mill surrounding the finished sample lamella on all four sides.

2. The method of claim 1, in which characterizing the material removal rate of the low energy focused ion beam further comprises measuring the beam current of the low energy focused ion beam and determining a calibrated beam current.

3. The method of claim 2, in which the dose of ions per area is dependent on the calibrated beam current, an area of the region in which the pattern is milled, and the predetermined pattern milling time used by the low energy focused ion beam.

4. The method of claim 1, in which the high energy focused ion beam and the low energy focused ion beam are emitted from the same focused ion beam column.

5. The method of claim 1, in which the high energy focused ion beam has a landing energy greater than eight kiloelectronvolts (8 keV).

6. The method of claim 1, in which the low energy focused ion beam has a landing energy less than eight kiloelectronvolts (8 keV).

7. The method of claim 1, in which the high energy focused ion beam has a landing energy greater than or equal to thirty kiloelectronvolts (30 keV).

8. The method of claim 1, in which the low energy focused ion beam has a landing energy between two and five kiloelectronvolts (2-5 keV).

9. The method of claim 1, in which milling the unfinished sample lamella with the low energy focused ion beam is performed without human intervention.

10. The method of claim 1, in which the focused ion beam is directed at an angle that is not parallel with the plane of the lamella.

11. The method of claim 1, in which the substrate comprises a single-crystalline material.

12. The method of claim 11, in which the single-crystalline material comprises silicon.

13. The method of claim 1, in which the focused ion beam is directed at a nonzero incident angle relative to the plane of the lamella.

14. The method of claim 13, in which the focused ion beam is directed at an angle relative to the plane of the lamella that is substantially forty-five (45) degrees.

15. The method of claim 13, in which the focused ion beam or the sample or both is rotated about an axis normal to the sample surface prior to milling the unfinished sample lamella.

16. The method of claim 1, further comprising:
producing a first set of one or more lamellae, each lamella in the set receiving a first specified dose of ions per area delivered by the low energy focused ion beam;
measuring one or more characteristics of the first set of lamellae at a point in time after or at a point in time during the process of milling the set of lamellae;
recording the one or more measured characteristics of first set of lamellae;
calculating a second specified dose of ions per area for the low energy focused ion beam based on the difference between an intended lamella characteristic and the one or more measured characteristics of the first set of lamellae;
producing a second set of one or more lamellae using a second pattern milling time to deliver the second specified dose of ions per area for the low energy focused ion beam.

17. The method of claim 16, in which a person manually observes the one or more characteristics of the first set of lamellae and the person provides an adjustment factor used in calculating the second specified dose.

18. The method of claim 16, in which a machine vision algorithm measures the one or more characteristics of the first set of lamellae, and the one or more measured characteristics of the first set of lamellae is used to calculate an adjustment factor used in determining the second specified dose.

19. A system for forming a transmission electron microscopy sample lamella comprising:
a focused ion beam column
a sample stage;
a sample disposed on or within the sample stage;
a programmable controller programmed with computer instructions that, when executed by a computer processor, causes the system to automatically:
direct a high energy focused ion beam toward a bulk volume of material, the bulk volume of material including a feature of interest and a volume of material to be removed, to mill away the volume of material to be removed;
mill away the volume of material to be removed with the high energy focused ion beam to produce an unfinished sample lamella having a thickness that is greater than the desired thickness of a finished sample lamella, one or more exposed faces of the unfinished sample lamella including a damage layer;
characterize the material removal rate of a low energy focused ion beam at a specified time prior to directing the low energy focused ion beam toward one or more of the exposed faces of the unfinished sample lamella;
subsequent to characterizing the material removal rate of the low energy focused ion beam, direct the low energy focused ion beam toward one or more of the exposed faces of the unfinished sample lamella for a predetermined pattern milling time to deliver a specified dose of ions per area from the low energy focused ion beam;
mill the one or more exposed faces of the unfinished sample lamella with the low energy focused ion beam to remove at least a portion of the damage layer, thereby producing the finished sample lamella including at least a portion of the feature of interest;
wherein causing the system to mill the one or more exposed faces of the unfinished sample lamella with the low energy focused ion beam includes performing a box mill by directing the low energy ion beam at an angle of incidence less than 90 degrees toward the one or more face of the unfinished sample lamella, the box mill having a size that is larger than the one or more faces of the finished sample lamella, and
in which the system characterizes the material removal rate of the low energy focused ion beam by measuring the material removal rate of the low energy focused ion beam.

20. The system of claim 19, in which the system characterizes the material removal rate of the low energy focused ion beam by measuring the beam current of the low energy focused ion beam and determining a calibrated beam current.

21. The system of claim 20, in which the dose of ions per area is dependent on the calibrated beam current, an area of the region in which the pattern is milled, and the predetermined pattern milling time used by the low energy focused ion beam.

22. The system of claim 19, in which the high energy focused ion beam has a landing energy greater than eight kiloelectronvolts (8 keV).

23. The system of claim 19, in which the low energy focused ion beam has a landing energy less than eight kiloelectronvolts (8 keV).

24. The system of claim 19, in which the low energy focused ion beam has a landing energy between two and five kiloelectronvolts (2-5 keV).

25. The system of claim 19, in which the programmable controller further causes the system to automatically:
produce a first set of one or more lamellae, each lamella in the set receiving a first specified dose of ions per area delivered by the low energy focused ion beam;
measure one or more characteristics of the first set of lamellae at a point in time after or at a point in time during the process of milling the set of lamellae;
record the one or more measured characteristics of first set of lamellae;
calculate a second specified dose of ions per area for the low energy focused ion beam based on the difference between an intended lamella characteristic and the one or more measured characteristics of the first set of lamellae;
produce a second set of one or more lamellae using a second pattern milling time to deliver the second specified dose of ions per area for the low energy focused ion beam.

26. The system of claim 25, in which a machine vision algorithm measures the one or more characteristics of the first set of lamellae, and the one or more measured characteristics of the first set of lamellae is used to calculate an adjustment factor used in determining the second specified dose.

27. The method of claim 1 wherein performing a box mill around the unfinished sample lamella with a size that is larger than the intended final thickness of the finished sample lamella includes automatically milling in a continuous operation without observing the progress of the mill until the specified dose of ions is delivered.

28. The system of claim 19 wherein performing a box mill around the unfinished sample lamella with a size that is larger than the intended final thickness of the finished sample lamella includes automatically milling in a continuous operation without observing the progress of the mill until the specified dose of ions is delivered.

* * * * *